United States Patent [19]

Gresens

[11] Patent Number: 4,704,806
[45] Date of Patent: Nov. 10, 1987

[54] APPARATUS FOR DETERMINING THE TIMEWISE PROGRESS OF THE DRYING OF A MATERIAL SAMPLE

[75] Inventor: Harry Gresens, Benningen, Fed. Rep. of Germany

[73] Assignee: Bruckner Trockentechnik GmbH & Co. KG, Leonberg, Fed. Rep. of Germany

[21] Appl. No.: 932,668

[22] Filed: Nov. 20, 1986

[30] Foreign Application Priority Data

Jan. 30, 1986 [DE] Fed. Rep. of Germany ....... 3602815

[51] Int. Cl.$^4$ ............................................. F26B 21/06
[52] U.S. Cl. ........................................... 34/54; 34/89
[58] Field of Search ....................... 34/54, 191, 34, 89, 34/218, 48

[56] References Cited

U.S. PATENT DOCUMENTS

| 3,131,034 | 4/1964 | Marsh | 34/54 |
| 3,233,334 | 2/1966 | Hamilton | 34/54 |
| 3,522,663 | 8/1970 | Grimmelt et al. | 34/54 |

Primary Examiner—Larry I. Schwartz
Attorney, Agent, or Firm—C. O. Marshall, Jr.

[57] ABSTRACT

The invention relates to apparatus for determining the timewise progress of the drying of a damp material sample. The material sample is continually connected to a movable part of a weighing mechanism during the drying process, and the delivery of the drying air stream can be interrupted in time with the weighing. Such apparatus facilitates automatic determination of the drying progress curve.

13 Claims, 7 Drawing Figures

APPARATUS FOR DETERMINING THE TIMEWISE PROGRESS OF THE DRYING OF A MATERIAL SAMPLE

BACKGROUND OF THE INVENTION

The invention relates to apparatus for determining the timewise progress of the drying of a damp material sample, comprising means for producing a drying air stream of defined temperature, flow quantity and moisture content, a retaining device for holding the material sample during the drying, a nozzle system for delivering the drying air stream to the material sample held by the retaining device, and means for intermittently weighing the material sample during the drying.

In drying technology the drying properties of the materials to be dried are generally an unknown quantity. Thus in the drying of textiles an extraordinarily large number of parameters influence the drying properties so that it is only possible to make an exact forecast of the drying properties after extensive preliminary tests. However, such preliminary tests involve a great deal of work and are therefore very costly.

It is known in the art for the timewise progress of the drying of a damp material sample to be determined approximately by drying the material sample in a testing arrangement and repeatedly during the drying process removing the sample from the testing arrangement and weighing it. However, such an operation is very complicated and time-consuming; in addition, the degree of accuracy which can be achieved in this way is very limited.

SUMMARY OF THE INVENTION

The object of the invention, therefore, is to avoid these shortcomings and to construct apparatus of the type set out above in such a way that the timewise progress of the drying of the damp material sample can be determined in a particularly simple manner and in particular that automation is made possible.

This object is achieved according to the invention by continually connecting a movable part of the weighing means to the retaining device during the drying, and intermittently interrupting the delivery of the drying air stream in time with the weighing by means of a controllable valve.

In the apparatus according to the invention the material sample remains in the drying apparatus during the entire drying process. In order for weighing of the material sample to be carried out, preferably repeatedly, during the drying process the retaining device which holds the material sample is connected to the movable part of the weighing arrangement.

Since the material sample is subjected to certain forces by the drying air stream delivered by the nozzle system, the delivery of this air stream is interrupted in time with the weighing by a controllable valve. In this way the material sample located in the drying apparatus can be weighed exactly during periodic brief interruptions of the drying air stream and in this way the timewise progress of the drying can be accurately determined.

DESCRIPTION OF A PREFERRED EMBODIMENT

The apparatus according to the invention for determining the timewise progress of the drying of a damp material sample contains a nozzle system 1 for delivery of a drying air stream of defined temperature, flow quantity and moisture content to a circular damp material sample which is held on a retaining device formed by a ring of pins 3.

Figure 3:
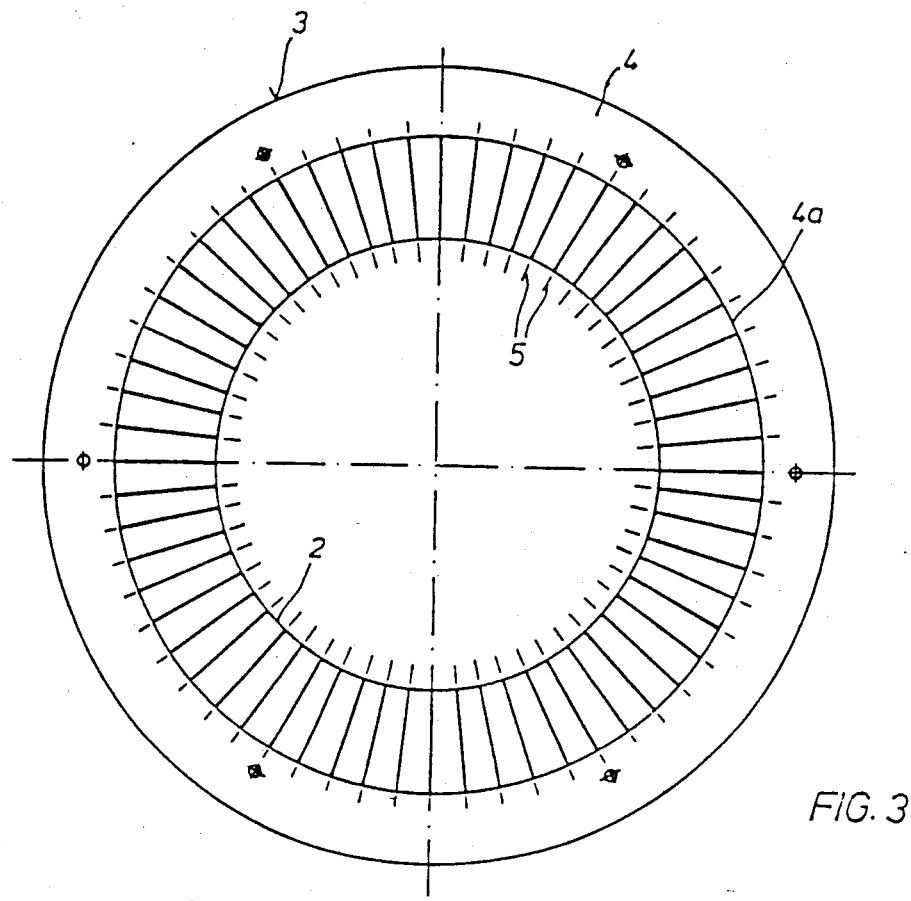
FIG. 3 shows a plan view of the ring of pins.

As can be seen in particular from FIG. 3, the ring of pins 3 consists of an annular pin holder 4 and a plurality of pins 5 which are directed inwards in the radial direction from the inner edge 4a of the pin holder 4 and end in an upwardly directed point 5a.

The cross-section of the pin holder 4 is streamlined (cf. FIG. 2) and the tapered end points outwards. The pin holder 4 consists of two parts 4c and 4d which are connected by screws 4b and between which the pins 5 are gripped.

The ring of pins 3 is supported on the ends 6a, 6b of a multi-armed bracket 6 (cf. FIG. 1) which forms the movable part of an electronic weighing arrangement. This bracket can for example have two or three supporting arms distributed in the peripheral direction.

Figure 6:
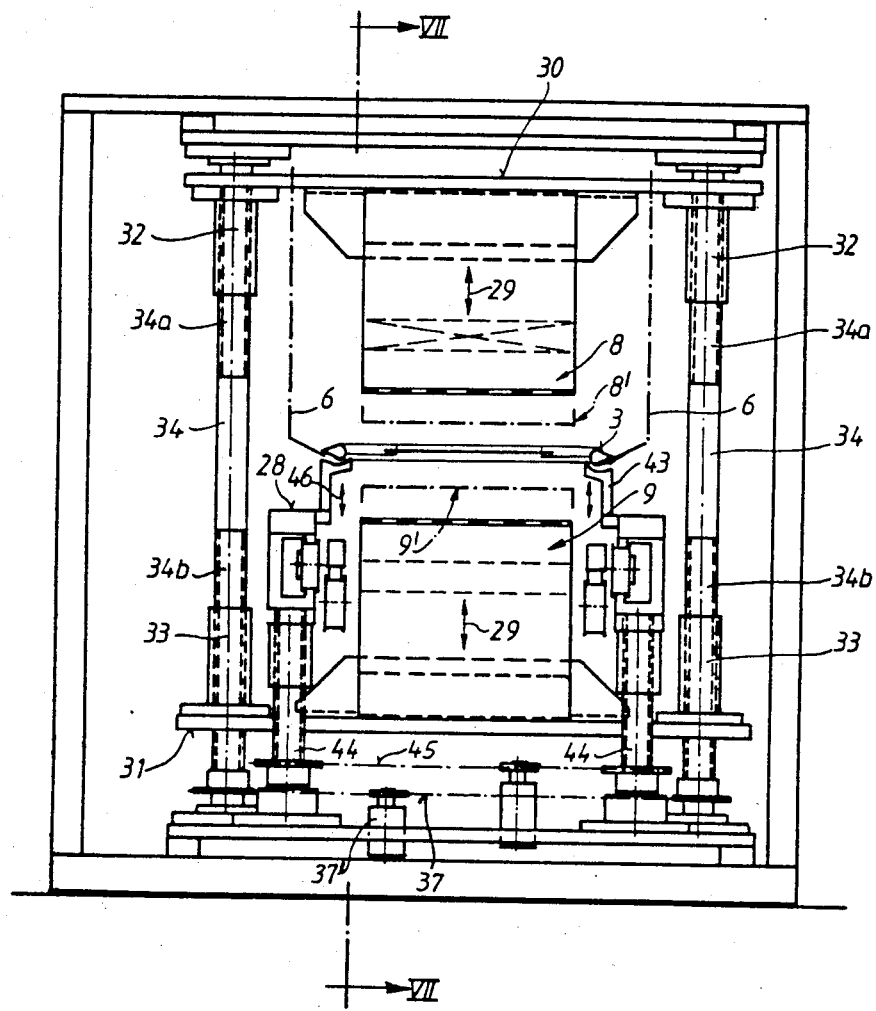
FIG. 6 shows a simplified front view of the assembled apparatus with nozzles which can be raised and lowered.
Figure 7:
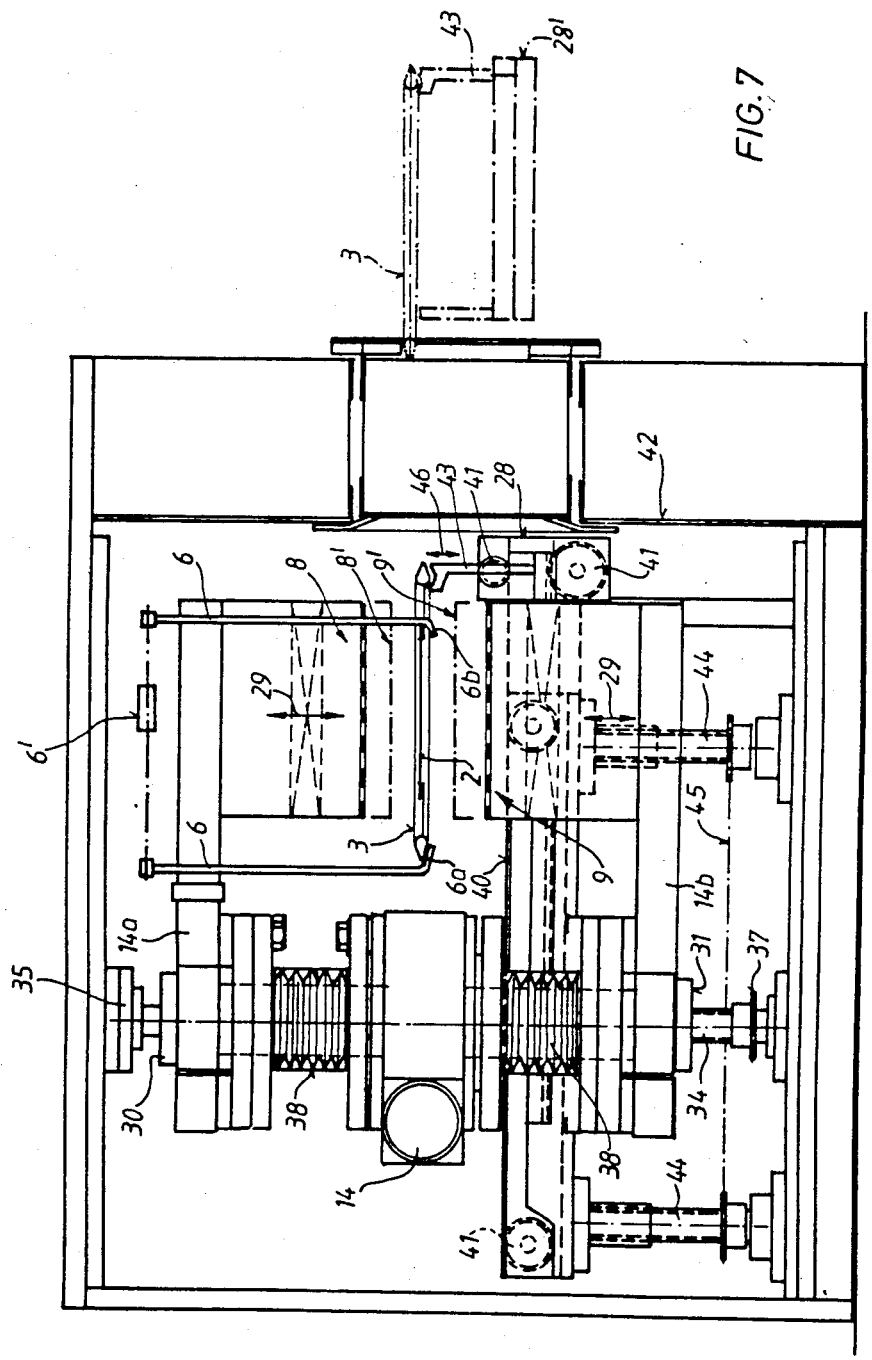
FIG. 7 shows a partial side view approximately along the line VII—VII in FIG. 6.

The ring of pins 3 can be inserted into the nozzle system 1 and let down on the multi-armed bracket 6 by means of a drawer 28 which is explained in greater detail with the aid of FIGS. 6 and 7.

Figure 1:
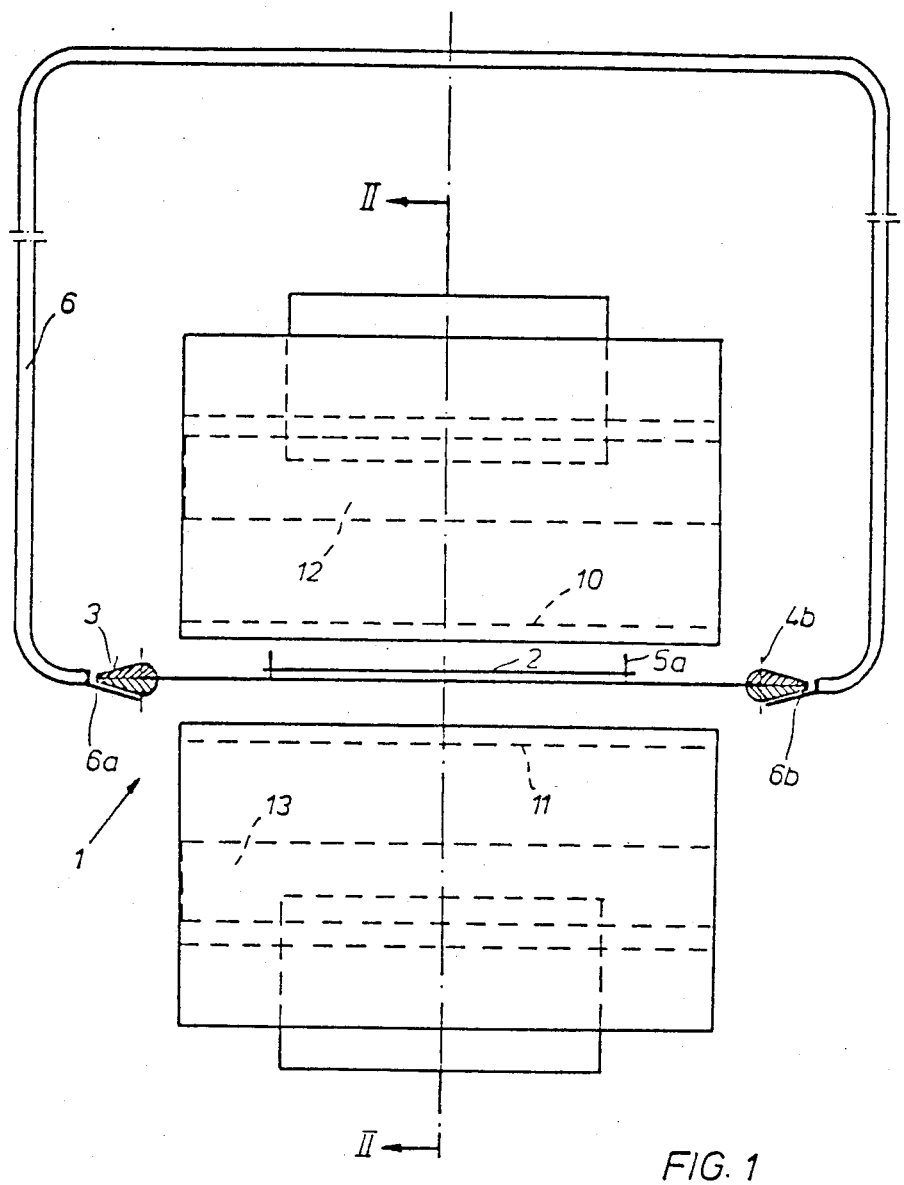
FIG. 1 shows a schematic end view of the apparatus according to the invention with its principal parts.
Figure 2:
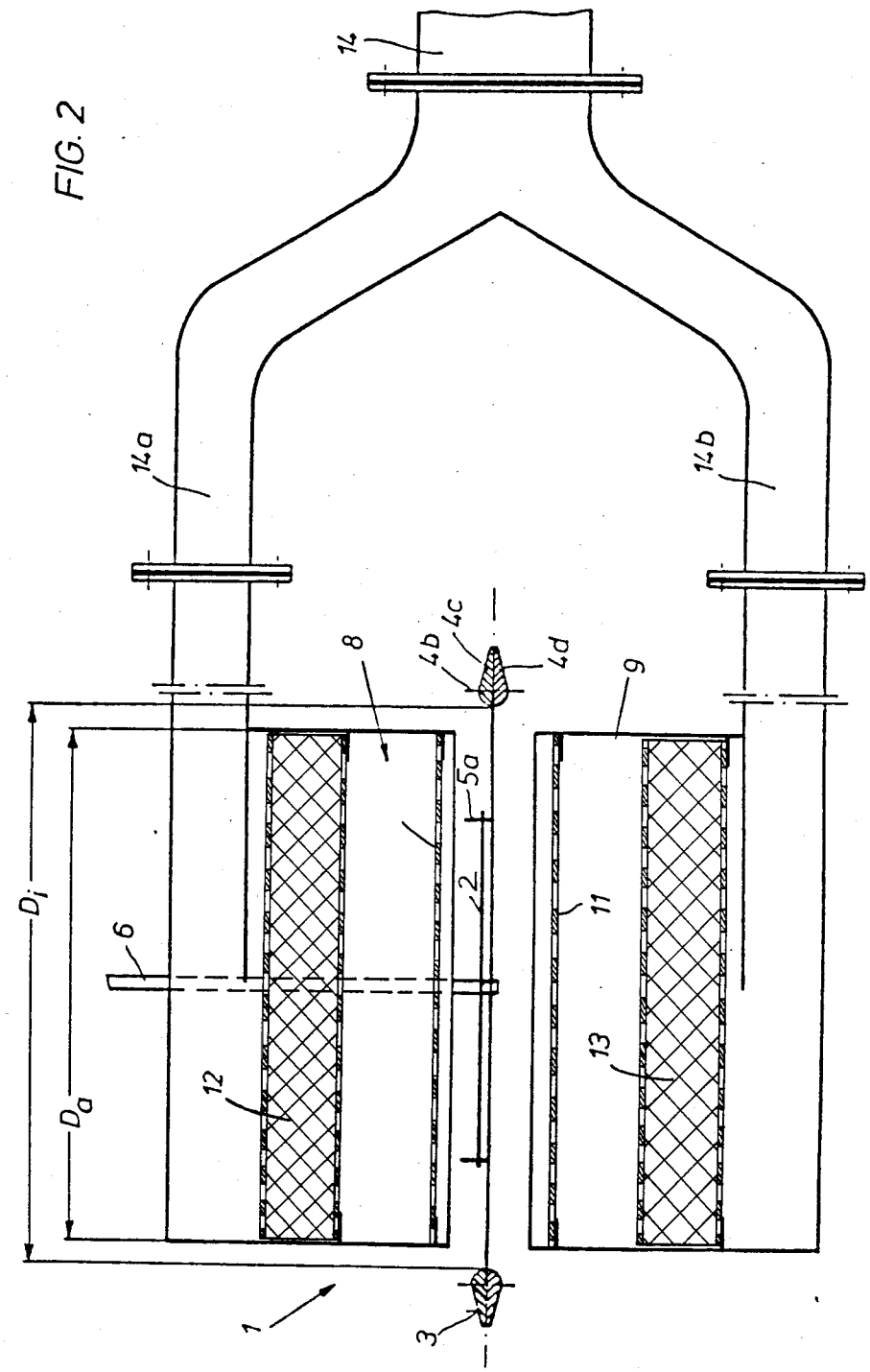
FIG. 2 shows a section along the line II—II in FIG. 1.

In the position illustrated in FIGS. 1 and 2 the ring of pins 3 with the material sample 2 is arranged symmetrically between the upper nozzles 8 and the lower nozzles 9 of the nozzle system 1. The upper and lower nozzles 8, 9 each contain a circular perforated disc 10 or 11 respectively and a preceding element 12 or 13 respectively of circular cross-section for equalisation of the air flow over the entire cross-section.

As can be seen from FIG. 2, the internal diameter $D_i$, of the ring of pins 3 is greater than the external diameter $D_a$ of the nozzle system 1. Consequently the pin holder 4 of the ring of pins 3 is located sufficiently far outside the edge of the material sample 2 and therefore does not restrict the smooth flow of the drying air stream onto the upper and lower faces of the material sample 2.

The drying air stream is delivered to the nozzle system 1 via a pipe 14 which is connected to the upper nozzles 8 and the lower nozzles 9 by branch pipes 14a, 14b respectively.

Figure 4:
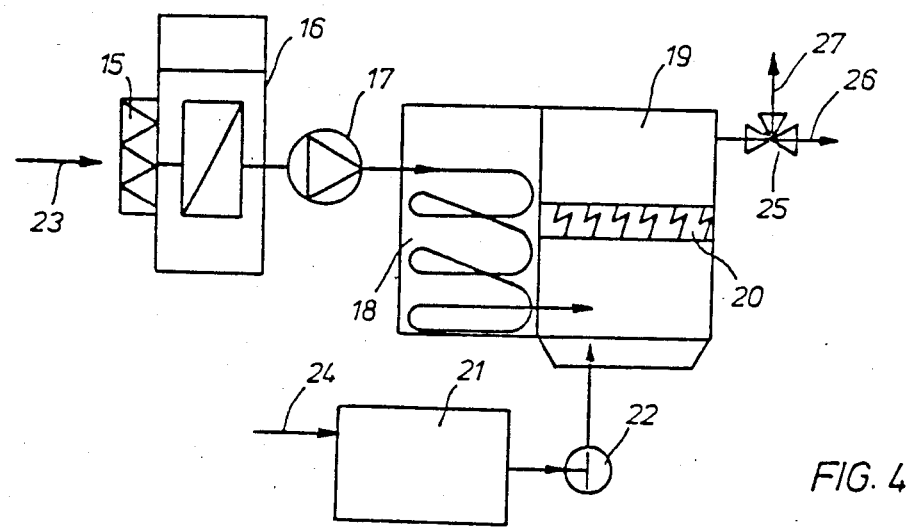
FIG. 4 shows a schematic representation of the arrangement for producing the drying air stream.

FIG. 4 shows quite schematically the essential parts of a preferred arrangement for producing the drying air stream of defined temperature, flow quantity and moisture content.

It contains a fresh air suction filter 15, an arrangement 16 which is preferably constructed as a cold compressed air dryer for complete drying of the air which is drawn in, a blower 17 (for example a lateral channel blower), a heat exchanger 18 (for example a thermal oil heated tubular heat exchanger), a moistening chamber 19 with a drip catcher 20 and a steam generator 21 which is connected via a steam regulating valve 22 to the moistening chamber 19.

The air which is drawn in is designated by the arrow 23, and the water delivered to the steam generator 21 is designated by the arrow 24.

Drying air of a defined temperature, flow quantity and moisture content is delivered to the nozzle system 1 (arrow 26 in FIG. 4) via a controllable valve 25 (for example a three-way valve) in one switch position of this valve. In the other switch position of the valve 25 the delivery of air to the nozzle system 1 is interrupted; in this case the air is led off via the valve 25 (arrow 27).

The apparatus according to the invention which is described above functions as follows:

The damp material sample 2 arranged in the nozzle system 1 is dried by means of the accurately conditioned drying air stream and periodically weighed. For the purpose of weighing the delivery of the air stream is interrupted in time with the weighing by the controllable valve 25.

An electronic weighing arrangement supplies an analogue or digital weighing signal for the sample weight. This signal is obtained as frequently as is required by a computer which runs the plant (and thus also controls the periodic switching of the valve 25) and stored. At the end of the drying process, when the measured value stops decreasing the measuring operation is halted. The computer then supplies a diagram of the timewise progress of the drying as is illustrated by way of example in FIG. 5.

The moisture content of the sample (in % by weight) is plotted in the ordinate and the drying time (in seconds) is plotted in the abscissa.

Figure 5:
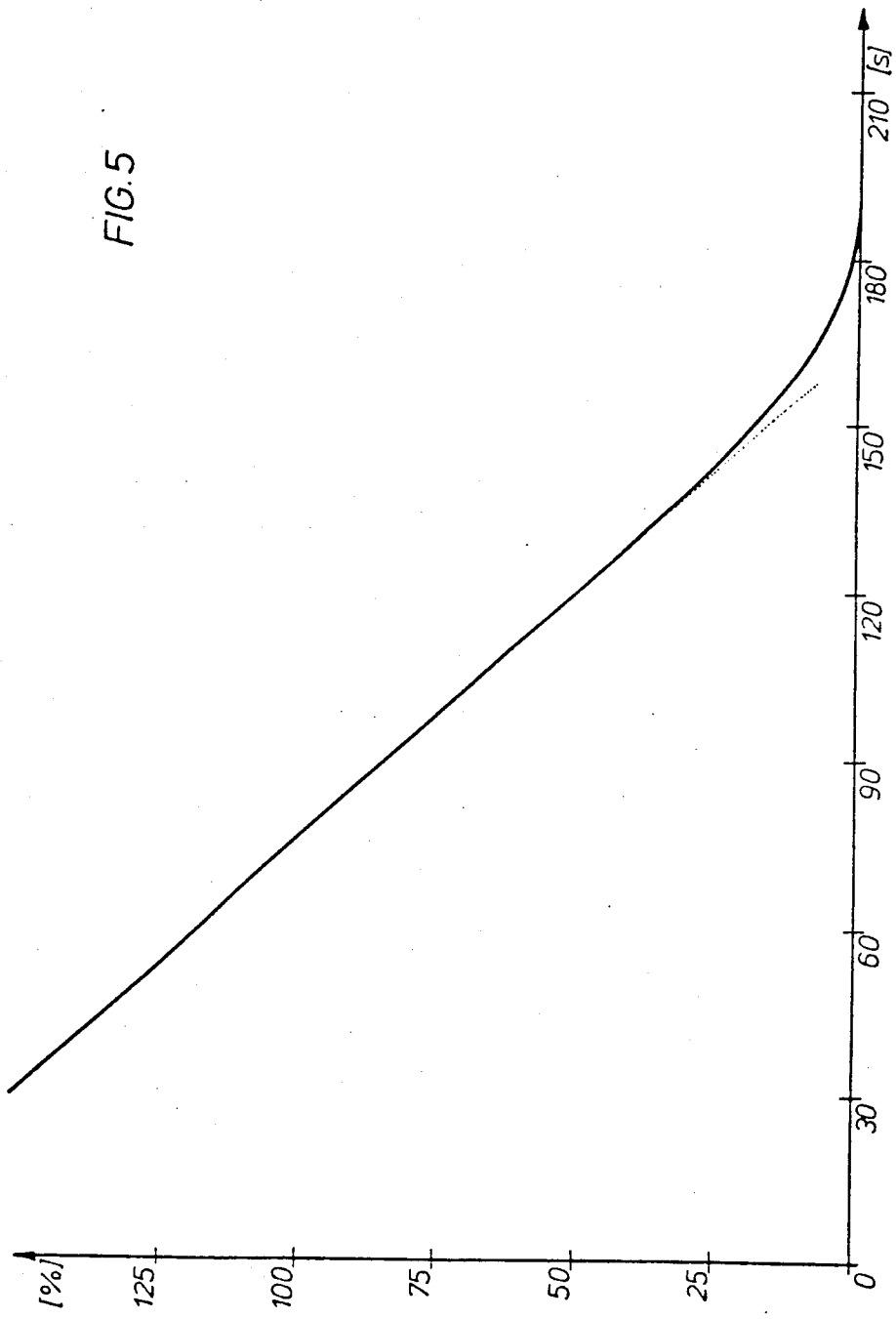
FIG. 5 shows a diagram of the timewise progress of the drying of a material sample.

In the drying example according to FIG. 5 the drying time was 89.5 seconds for drying from 100% to 8%. The nozzle pressure was 550 Pa, the air temperature 20°, the weighing time (in total) 3 seconds.

By means of suitable computer programs it is possible to infer the drying conditions in a real tensioning machine from drying progress data according to FIG. 5 (on the basis of the nozzle geometry in the testing arrangement and the other parameters of the heat and material exchange. In the simplest case the testing arrangement which determines the temperature progress curve is set so that the coefficient of heat transfer corresponds to that of the real machine, and the physical drying conditions (temperature and moisture content of the air) are also adapted to the original drying situation. In this case it is possible to infer the drying conditions to be expected in the real dryer directly from the drying progress curve.

On the other hand, if it is not possible for the coefficients of heat transfer and/or the physical limiting conditions of the drying process in the real dryer to be simulated in the testing arrangement, then various calculations using analogies are also necessary in order to infer the drying speed to be expected in the real machine from the drying progress curve according to FIG. 5 determined in the testing arrangement. In the present context the calculations to be carried out by means of computers will not be gone into any further.

With the apparatus according to the invention drying progress curves for any materials (between 30 and 300 g/m$^2$) can be obtained automatically at different temperatures, different air speeds in the nozzles and different moisture contents of the air. The nozzles can be constructed in such a way that coefficients of heat transfer of up to 200 W/m$^2$ can be produced.

The absolute symmetry of the air supply and discharge means ensures that the air flows off in a clean, almost laminar fashion.

The controllable valve 25 is constructed in such a way that the shutting off and reconnection of the air stream (in time with the weighing) takes place quite smoothly in practice.

The air temperature, the moisture content of the air and the nozzle pressure are determined using suitable measuring elements and kept constant with self-adapting regulators.

Although in the preceding description of the embodiment and the way in which it functions it has been assumed that the weighing arrangement used is constructed for repeated weighing of the material sample during the drying process, it is also possible to construct this weighing arrangement for continuous weighing of the material sample during the drying process.

In this connection it may be presupposed that the valve for interrupting the air stream at the time of weighing can only be used when the drying of the material sample permits an interruption of the air stream. On the other hand, if the drying only takes a short time (e.g. within 1–3 seconds), then the switching time in this case is too long to obtain a sufficient number of weighings from which it is possible to derive a drying progress curve. Therefore, for material samples which dry so rapidly it is advantageous for the measurement signal from the weighing arrangement to be picked up continuously as an analogue signal (with the weighing arrangement constructed appropriately for continuous weighing) and for it to be freed later of signal noise by mathematical methods. A drying progress curve can also be plotted by means of this analogue signal.

In the preferred arrangement for producing the drying air stream of a defined temperature, flow quantity and moisture content as described above an arrangement 16 is used for complete drying of the air which is drawn in. However, in many cases this arrangement 16 can be omitted, particularly if it is possible to dispense with the influence of the temperature and/or moisture content in obtaining the drying progress curves.

In the construction and functioning of the apparatus according to the invention as explained above with the aid of FIGS. 1 to 4 and with the aid of the diagram according to FIG. 5 the timewise progress of the drying of a damp material sample is determined in particular by the manner of the delivery of the drying air, i.e. the drying air is delivered to the material sample 2 via the controllable valve 25 with a defined temperature, flow quantity and moisture content and if required also with the possibility of a speed variation provided by perforated discs 10 and 11 which act as perforated shutters. However, this way of determining the timewise progress of the drying can be further refined or improved in order to be able to adapt specific coefficients of heat transfer even better to the particular nature of the material sample. As will be explained below with the aid of FIGS. 6 and 7, this can be achieved in the most favourable manner by retaining the upper and lower nozzles 8, 9 so that their vertical distance from the material sample 2 (cf. double arrows 29) can be adjusted synchronously and vertically in opposite directions.

The upper nozzles 8 and the lower nozzles 9 together with their appertaining branch pipes 14a and 14b respectively for the delivery of air are retained for the aforesaid purpose for example on mounting plates 30 and 31 respectively which in turn are held via threaded sleeves 32 and 33 respectively on a plurality of common threaded spindles 34 which are rotatably mounted above and below in housing bearings 35 and 36 respectively.

The threaded spindles 34 which act as adjusting spindles have counterrotating threaded sections 34a and 34b respectively on their upper and lower ends. In addition, these threaded spindles 34 can be driven synchronously, that is to say all at the same time and at the same speed, and for this purpose a common chain drive 37 with a drive motor 37' can be associated for example with these threaded spindles 34, as indicated particularly in FIG. 6.

Because of the way in which the upper and lower nozzles 8, 9 are mounted and are capable of being raised and lowered, they can be adjusted in their vertical distance with respect to the material sample 2 synchronously and in opposite directions, as is indicated in FIGS. 6 and 7 by the double arrows 29 and the positions 8' and 9' shown by dot-dash lines.

FIG. 7 shows a further possibility of building flexible sections into the branch pipes 14a and 14b which take the drying air streams to the upper and lower nozzles 8, 9 in order to take account of the upward and downward movements of the upper and lower nozzles 8, 9. For this purpose elastic hose-type bellows (for example metal bellows) 38 which are of a construction which is known per se and permit lengthening or shortening of the branch pipes 14a and 14b in the said sections can be arranged in the branch pipes 14a and 14b, particularly in the vertical sections thereof.

As has already been indicated above in the explanations relating to FIGS. 1 to 3, it is advantageous for the ring of pins 3 to be introduced between the upper and lower nozzles 8, 9 by means of a drawer 28 and to be laid loosely on a multi-armed bracket 6 belonging to the movable part of the weighing arrangement 6'. This can also be seen from FIGS. 6 and 7.

The drawer 28 is guided in a housing guide 40 and by means of rollers 41 in such a way that from the drawn-out position 28' which is shown by dot-dash lines in FIG. 7 and in which it is drawn out from the housing of the apparatus it can be pushed into its pushed-in position inside the housing 42 in which a ring of pins 3 which in the drawn-out position of the drawer 28 rests loosely on the upright supports 43 is pushed accurately into its operating position with respect to the bracket 6 and between the upper and lower nozzles 8, 9. When the drawer 28 and with it the ring of pins 3 with the material sample 2 have reached the aforementioned pushed-in position the drawer 28 can also be lowered with the aid of a worm drive 44 so that the ring of pins 3 which until then was carried loosely by the supports 43 rests loosely on the lower ends 6, 6b of the multi-armed bracket 6 of the electronic weighing arrangement 6'. The worm drive 44 can also be operated synchronously via a chain drive, as indicated at 45. As can be seen from FIGS. 6 and 7, the drawer 28 can contain a plurality of supports 43 distributed approximately in the peripheral direction of the ring of pins 3. In the pushed-in position the drawer 28 can then be lowered in the vertical direction (double arrow 46) out of the displacement position in which the ring of pins 3 rests loosely on the upper ends of the supports 43 into a waiting position in which the ring of pins 3 is raised from the supports 43 by the multi-armed bracket 6 of the weighing arrangement 6'.

I claim:

1. Apparatus for determining the timewise progress of the drying of a damp material sample (2), comprising means for producing a drying air stream of defined temperature, flow quantity and moisture content, a retaining device (3) for holding the material sample during the drying, a nozzle system (1) for delivering the drying air stream to the material sample held by the retaining device, and means for intermittently weighing the material sample wherein the improvement comprises a movable weight-sensing part (6) of the weighing means which is connected to support the retaining device (3) continually during the drying, and means (25) for intermittently interrupting the delivery of the drying air stream to the material sample in time with the intermittent weighing of the material sample.

2. Apparatus as claimed in claim 1, in which the nozzle system (1) comprises upper and lower nozzles (8, 9) between which the retaining device (3) for the material sample (2) is arranged, characterised in that the retaining device is formed by a ring of pins (3) which is arranged symmetrically between the upper and lower nozzles (8, 9).

3. Apparatus as claimed in claim 2, characterised by the following features:
   (a) the ring of pins (3) consists of an annular pin holder (4) and a plurality of pins (5) which are directed inwards in the radial direction on the inner edge (4a) of the pin holder and end in an upwardly directed point (5a).
   (b) the internal diameter (Di) of the pin holder (4) is greater than the external diameter (Da) of the nozzle system (1).

4. Apparatus as claimed in claim 3, characterised in that the cross-section of the pin holder (4) is streamlined and the tapered end points outwards.

5. Apparatus as claimed in claim 1, characterised in that the means for interrupting the delivery of the drying air stream comprises a controllable three-way valve.

6. Apparatus as claimed in claim 1, characterised in that the means for producing a drying air stream of defined temperature, flow quantity and moisture content contains the following components:
   (a) a blower (17),
   (b) a heat exchanger (18),
   (c) a moistening chamber (19) with a drip catcher (20),
   (d) a steam generator (21) connected via a steam regulating valve (22) to the moistening chamber (19).

7. Apparatus as claimed in claim 6, characterised in that the means for producing the drying air stream also contains an arrangement (16) for complete drying of the air.

8. Apparatus as claimed in claim 2, characterised in that the upper and lower nozzles (8, 9) each contain a circular perforated disc (10, 11) and preceding element (12, 13) serving for equalisation of the air flow over the entire cross-section.

9. Apparatus as claimed in claim 8, characterised in that the vertical distance of the upper and lower nozzles (8, 9) from the material sample (2) can be adjusted synchronously and vertically in opposite directions.

10. Apparatus as claimed in claim 9, characterised in that the upper and lower nozzles (8, 9) are held by mountings (30, 31) on a plurality of common adjusting spindles (34) so that they can be raised and lowered, and the said spindles have counterrotating threaded sections (34a, 34b) and can be driven synchronously.

11. Apparatus as claimed in claim 9, characterised in that flexible sections, particularly elastic hose-type bellows (38), are arranged in pipes (14a, 14b) which take the drying air streams to the upper and lower nozzles (8, 9).

12. Apparatus as claimed in claim 2, characterised in that the ring of pins (3) can be introduced between the upper and lower nozzles (8, 9) by means of a drawer (28) and can be laid loosely on a multi-armed bracket (6) belonging to the movable part of the weighing means.

13. Apparatus as claimed in claim 12, characterised in that the drawer (28) has a plurality of upright supports (43) for the ring of pins distributed approximately in the peripheral direction of the ring of pins (3) and can be lowered in the vertical direction out of a displacement position in which the ring of pins (3) rests loosely on the upper ends of the supports into a waiting position in which the ring of pins is raised from the supports by the multi-armed bracket (6) of the weighing means.

* * * * *